(12) United States Patent
Nakamura et al.

(10) Patent No.: US 10,517,461 B2
(45) Date of Patent: Dec. 31, 2019

(54) FLEXIBLE TUBE INSERTION APPARATUS

(71) Applicant: OLYMPUS CORPORATION, Tokyo (JP)

(72) Inventors: Shuji Nakamura, Akishima (JP); Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 48 days.

(21) Appl. No.: 15/838,441

(22) Filed: Dec. 12, 2017

(65) Prior Publication Data

US 2018/0098682 A1    Apr. 12, 2018

Related U.S. Application Data

(63) Continuation of application No. PCT/JP2015/067083, filed on Jun. 12, 2015.

(51) Int. Cl.
*A61B 5/00* (2006.01)
*A61B 1/00* (2006.01)
(Continued)

(52) U.S. Cl.
CPC .......... *A61B 1/00006* (2013.01); *A61B 1/008* (2013.01); *G02B 23/2476* (2013.01);
(Continued)

(58) Field of Classification Search
CPC ......... A61B 1/00; A61B 1/005; A61B 1/0052; A61B 1/0055; A61M 16/0418; A61M 2205/583; A61M 25/0041
(Continued)

(56) References Cited

U.S. PATENT DOCUMENTS 3,625,200 A * 12/1971 Muller ................. A61B 1/0055
600/585
6,327,492 B1 * 12/2001 Lemelson ...... A61B 17/320758
600/434
(Continued)

FOREIGN PATENT DOCUMENTS

JP    H06-70879 A    3/1994
JP    H06-181882 A    7/1994
(Continued)

OTHER PUBLICATIONS

International Search Report dated Sep. 8, 2015 issued in PCT/JP2015/067083.
(Continued)

*Primary Examiner* — May A Abouelela
(74) *Attorney, Agent, or Firm* — Scully, Scott, Murphy & Presser, P.C.

(57) ABSTRACT

A flexible tube insertion apparatus includes an insertion section including a plurality of segments, a plurality of stiffness variable portions provided in the respective segments and configured to vary stiffness of the respective segments, and a state detector configured to detect a shape of the insertion section. The apparatus includes a state calculator configured to acquire a shape of a tube at a time when the insertion section advances into the tube, and configured to calculate a relative position of the segment to the tube, and a control device configured to control, based on the shape of the tube, the stiffness variable portion provided in the segment which is calculated the relative position to the tube by the state calculator.

5 Claims, 13 Drawing Sheets

(51) Int. Cl.
*A61B 1/008* (2006.01)
*G02B 23/24* (2006.01)
*A61B 1/005* (2006.01)
*A61B 1/05* (2006.01)
*A61B 1/06* (2006.01)

(52) U.S. Cl.
CPC ............... *A61B 1/0053* (2013.01); *A61B 1/05* (2013.01); *A61B 1/0676* (2013.01); *G02B 23/2461* (2013.01)

(58) Field of Classification Search
USPC .......................................... 600/585, 141, 152
See application file for complete search history.

(56) References Cited

U.S. PATENT DOCUMENTS

| | | | | |
|---|---|---|---|---|
| 7,682,319 | B2* | 3/2010 | Martin | A61B 17/00234 600/139 |
| 8,214,083 | B2* | 7/2012 | Kawai | A61B 1/00147 600/118 |
| 8,246,575 | B2* | 8/2012 | Viola | A61B 1/00147 604/95.04 |
| 8,827,894 | B2* | 9/2014 | Belson | A61B 1/0053 600/114 |
| 8,845,524 | B2* | 9/2014 | Belson | A61B 1/0053 600/152 |
| 9,585,651 | B2* | 3/2017 | Lam | A61B 17/0401 |
| 9,901,410 | B2* | 2/2018 | Oyola | A61B 90/50 |
| 9,972,082 | B2* | 5/2018 | Holsing | A61B 5/061 |
| 9,980,778 | B2* | 5/2018 | Ohline | A61B 1/005 |
| 2003/0233058 | A1* | 12/2003 | Ewers | A61B 1/0008 600/585 |
| 2004/0254450 | A1* | 12/2004 | Griffin | A61M 25/00 600/411 |
| 2006/0178562 | A1* | 8/2006 | Saadat | A61B 1/0055 600/142 |
| 2006/0200000 | A1* | 9/2006 | Sato | A61B 1/0055 600/146 |
| 2007/0135683 | A1* | 6/2007 | Bob | A61B 1/00082 600/144 |
| 2007/0219529 | A1* | 9/2007 | Abe | A61M 25/0028 604/528 |
| 2011/0065993 | A1* | 3/2011 | Belson | A61B 1/0053 600/141 |
| 2011/0251519 | A1* | 10/2011 | Romoscanu | A61M 25/0013 600/585 |
| 2013/0303945 | A1* | 11/2013 | Blumenkranz | A61M 25/0067 600/585 |
| 2014/0166718 | A1* | 6/2014 | Swayze | A61B 17/1155 227/175.1 |
| 2018/0214138 | A9* | 8/2018 | Prisco | A61B 17/00 |

FOREIGN PATENT DOCUMENTS

JP          2001-170000 A       6/2001
WO     WO 2005/102144 A1     11/2005

OTHER PUBLICATIONS

English translation of International Preliminary Report on Patentability dated Dec. 21, 2017 together with the Written Opinion received in related International Application No. PCT/JP2015/067083.

* cited by examiner

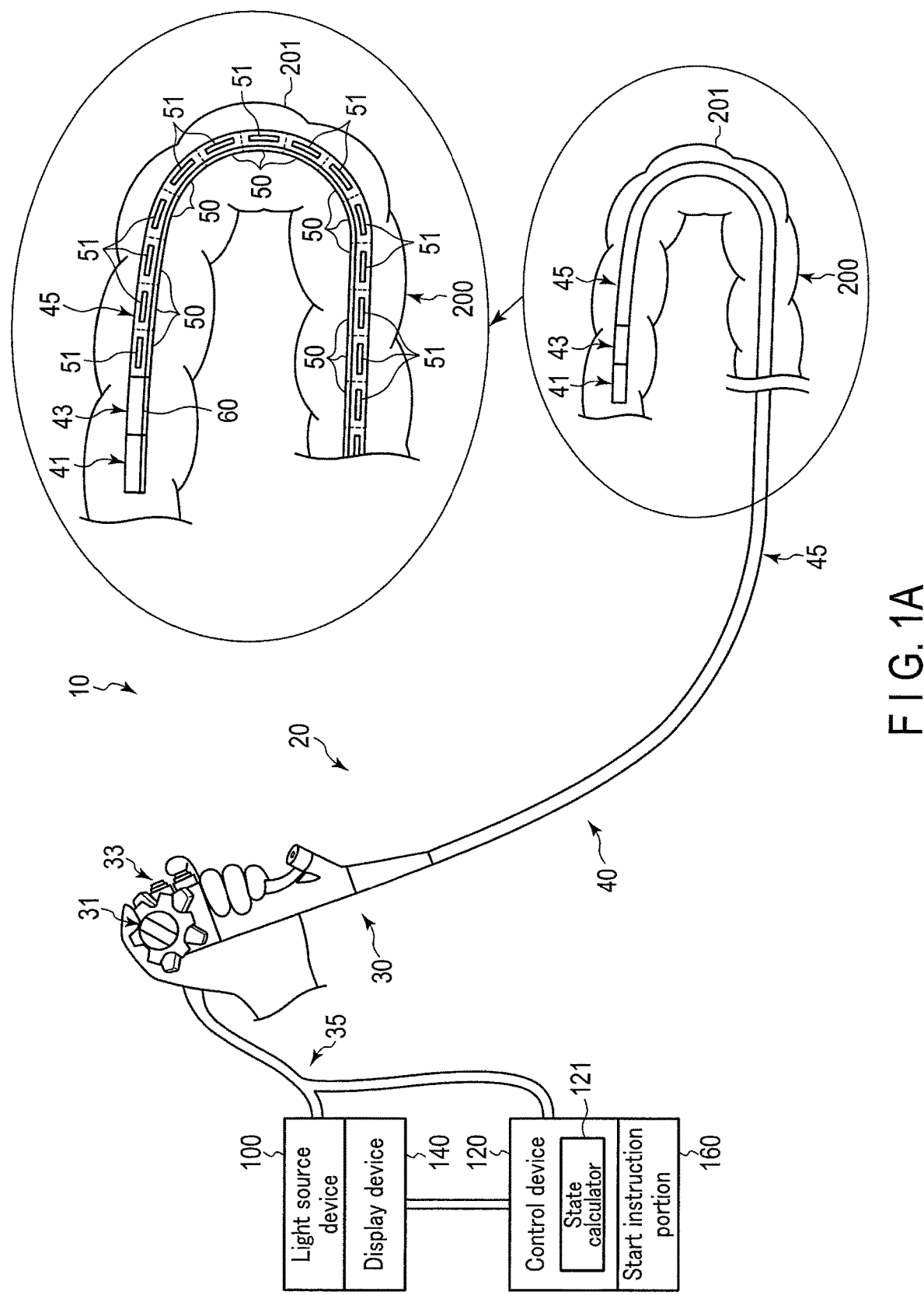
F I G. 1A

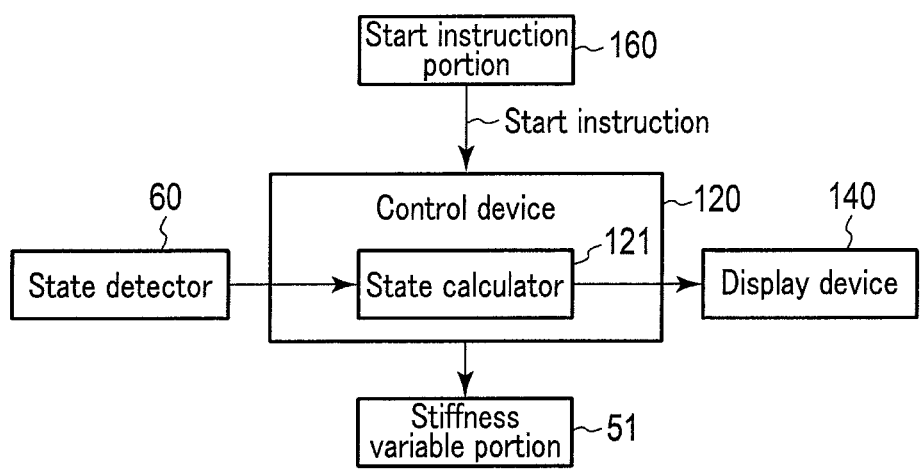
F I G. 1B

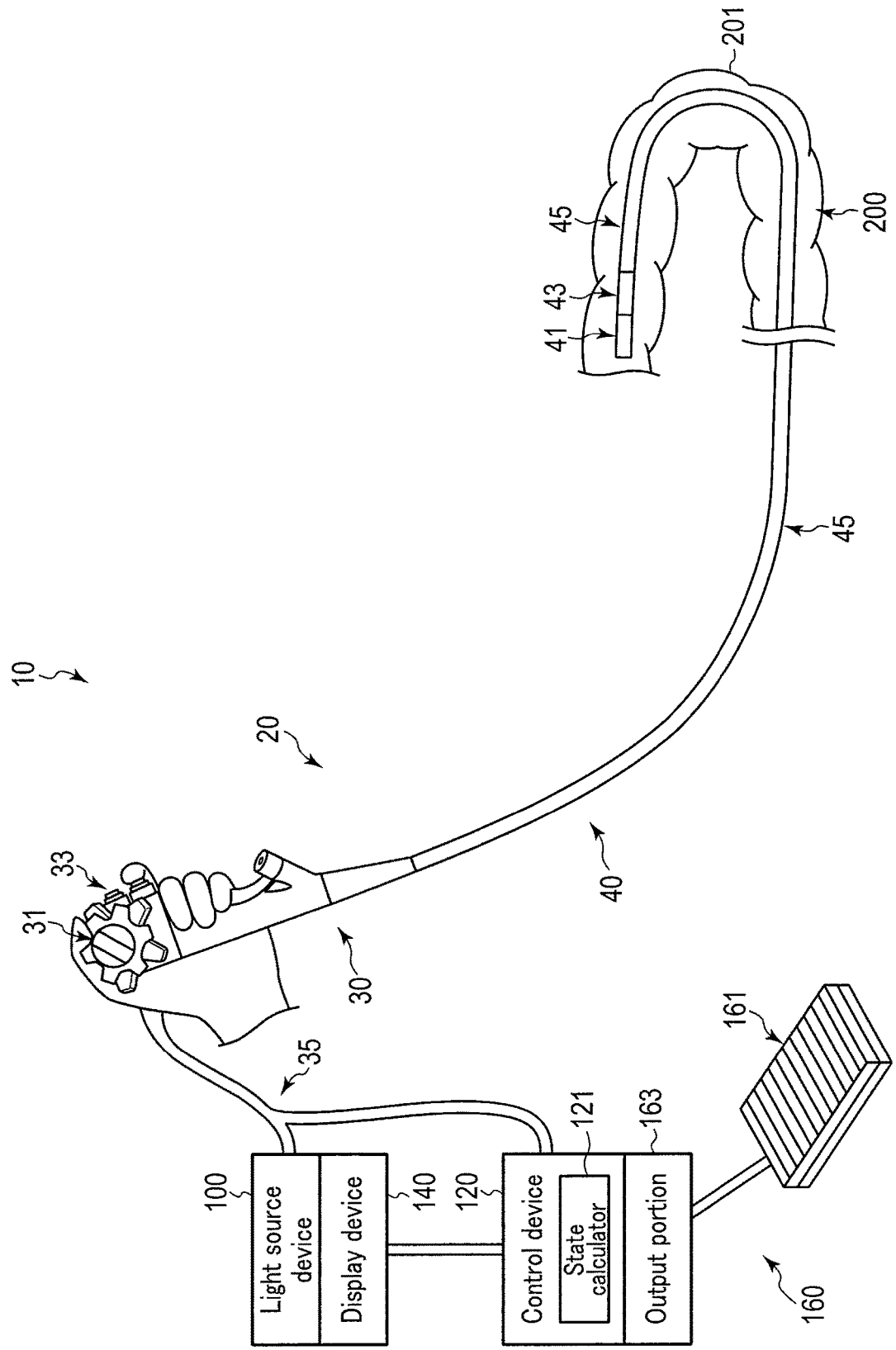
F I G. 3A

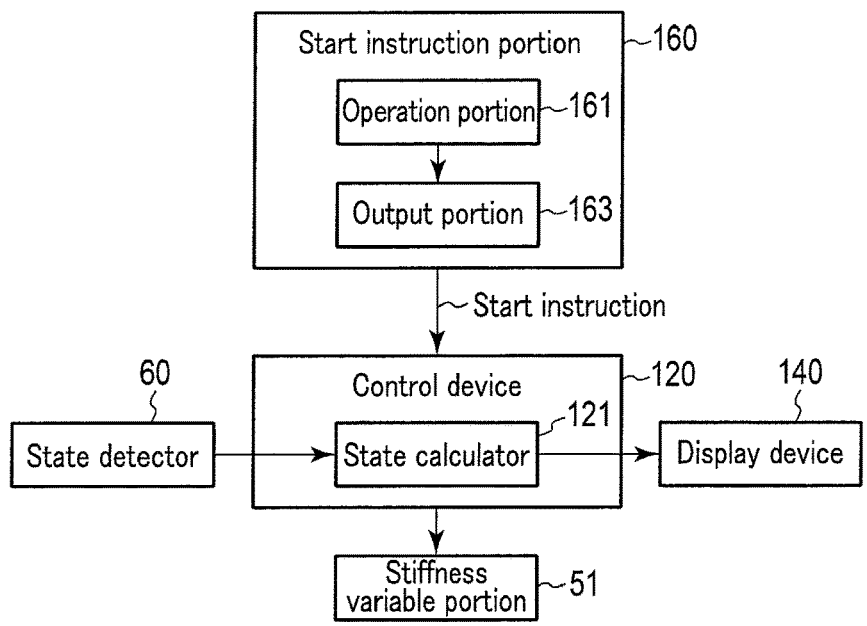
F I G. 3B
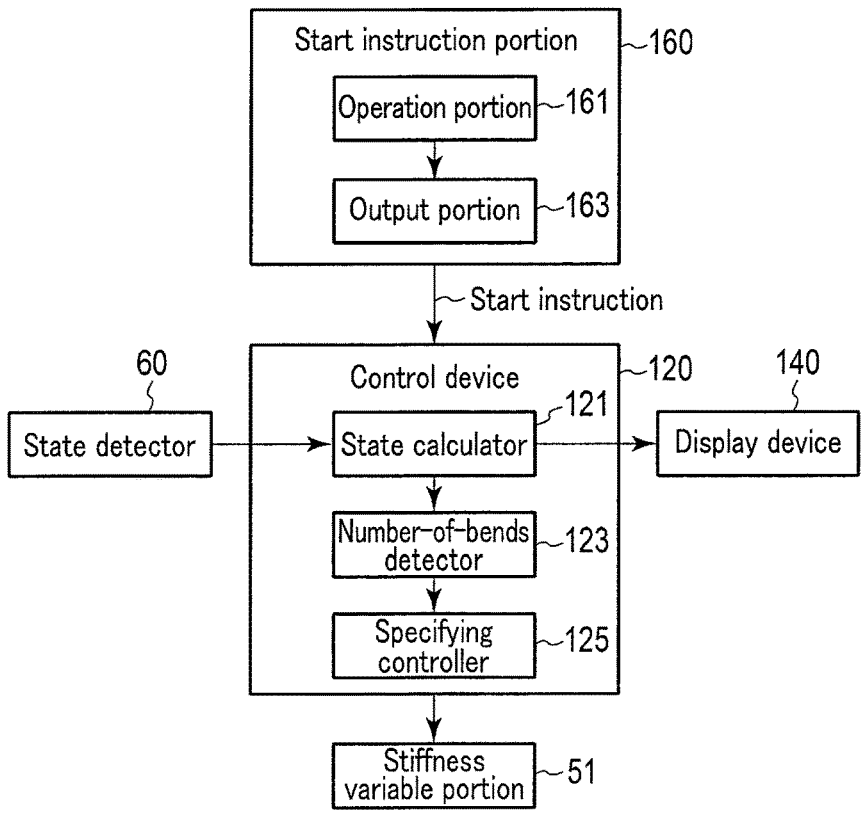
F I G. 4

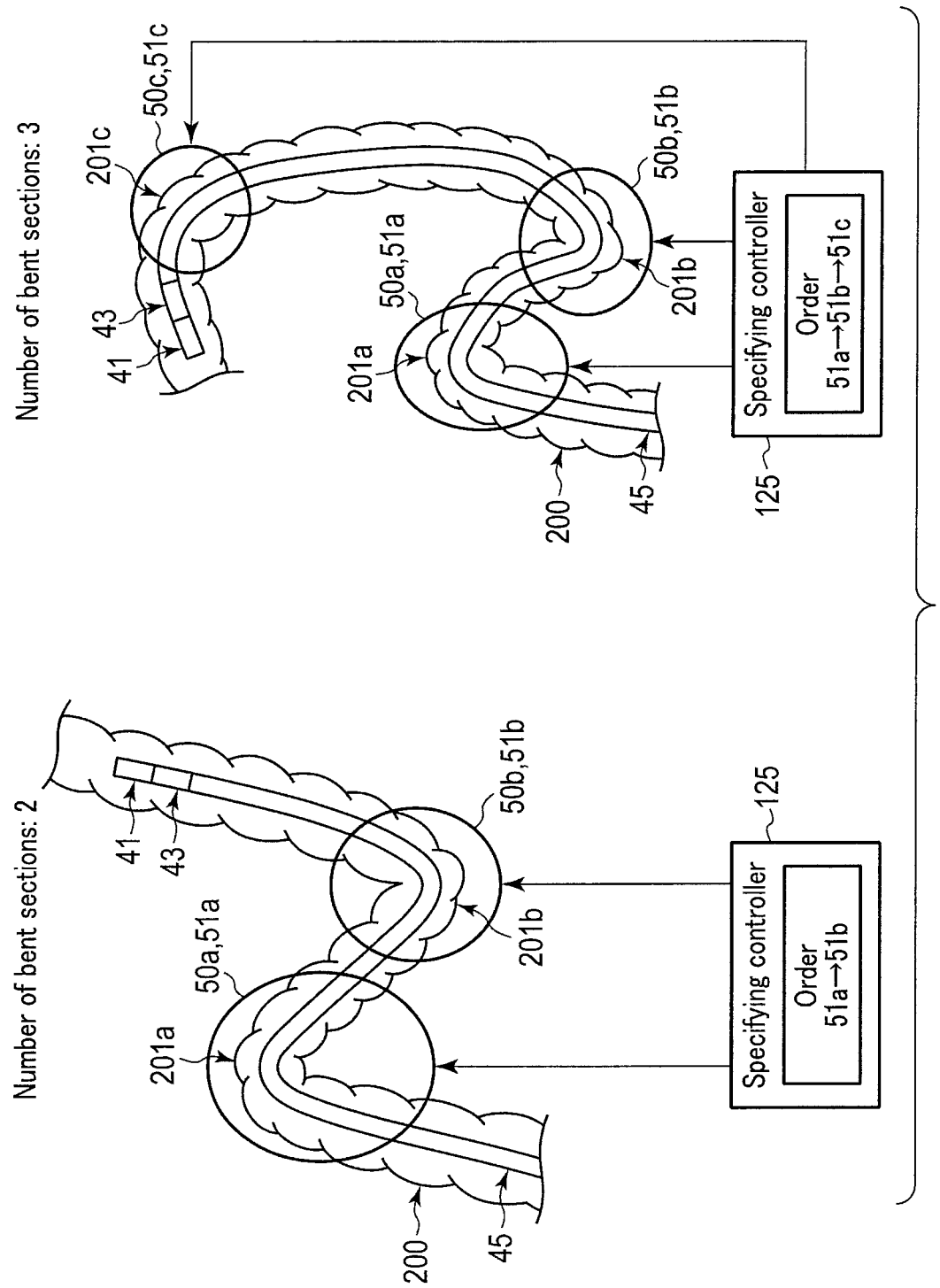
F I G. 5A

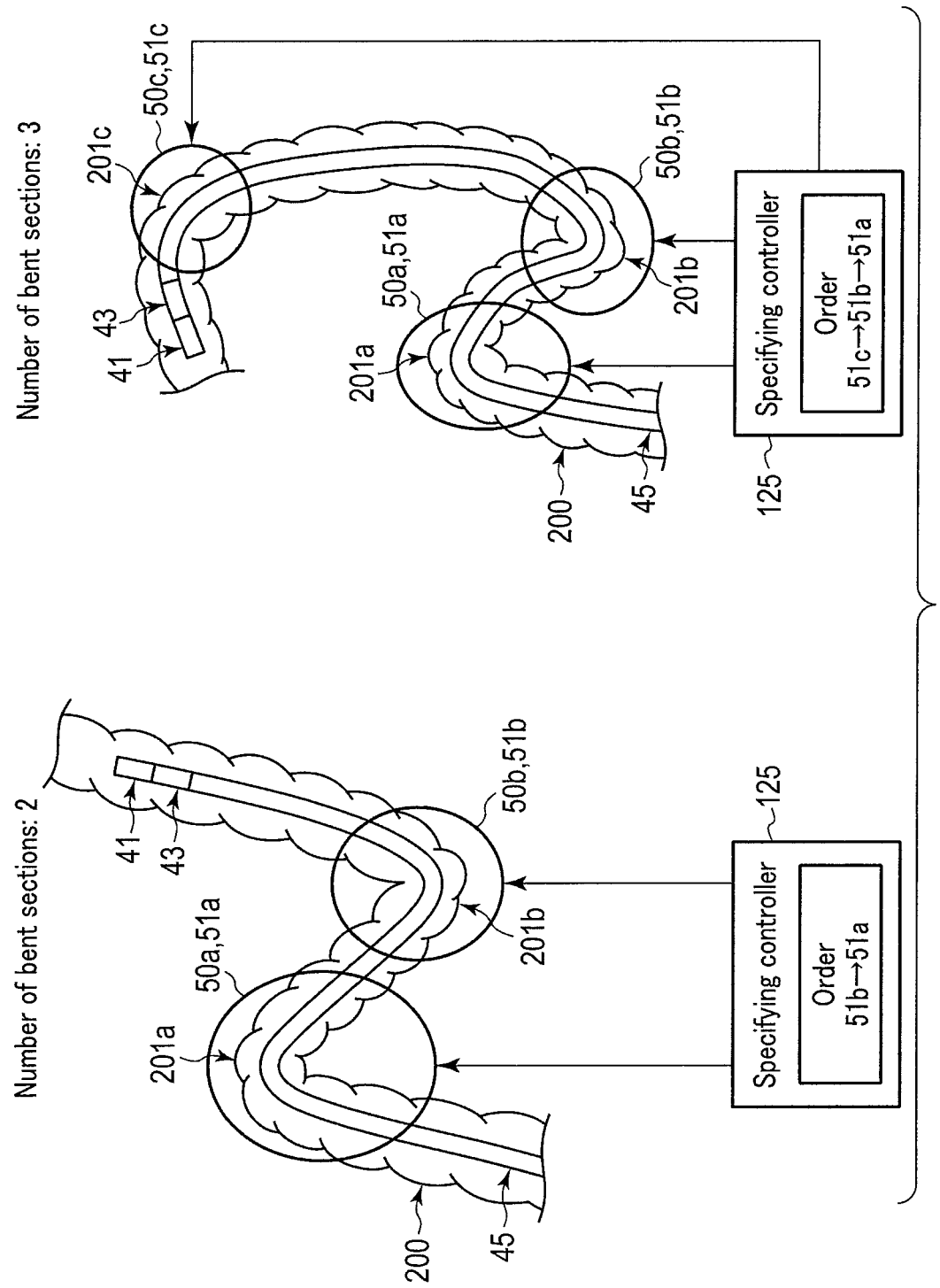
F I G. 5B

| Time instant | | T0 | T1 | T2 | T3 | T4 | T5 | T6 | T7 | T8 | T9 |
|---|---|---|---|---|---|---|---|---|---|---|---|
| Insertion section 40 | | Advancing | Stuck | Advancing | Advancing | Stuck | Advancing | Advancing | Stuck | Advancing | Advancing |
| Variation of stiffness | Bent section 201a | OFF | OFF | ON | ON | ON | ON | ON | ON | ON | ON |
| | Bent section 201b | OFF | OFF | OFF | OFF | OFF | ON | ON | ON | ON | ON |
| | Bent section 201c | OFF | OFF | OFF | OFF | OFF | OFF | OFF | OFF | ON | ON |

FIG. 8A

FLEXIBLE TUBE INSERTION APPARATUS

CROSS-REFERENCE TO RELATED APPLICATIONS

This application is a Continuation Application of PCT Application No. PCT/JP2015/067083, filed Jun. 12, 2015, the entire contents of all of which are incorporated herein by reference.

BACKGROUND OF THE INVENTION

1. Field of the Invention

The present invention relates to a flexible tube insertion apparatus.

2. Description of the Related Art

For example, in an endoscope system disclosed in Jpn. Pat. Appln. KOKAI Publication No. H6-70879, a flexible, elongated insertion section is inserted into a tube such as the large intestine, and the inside of the tube is observed by using an imaging element provided at a distal end of the insertion section.

In this endoscope system, a location where the flexibility of a flexible tube provided in the insertion section is selected based on insertion patterns in the past, and the flexibility of the flexible tube is partly varied. Besides, the selection of the location where the flexibility is varied is executed by an operator's remote operation. For example, the ease in insertion of the insertion section into the large intestine in an endoscopic examination is improved and the load on the operator and patient is reduced by the selection of the location where the flexibility is varied, which is based on the insertion patterns in the past, and by the partial variation of the flexibility.

BRIEF SUMMARY OF THE INVENTION

One embodiment of the present invention is a flexible tube insertion apparatus comprising an insertion section including a plurality of segments arranged along an axial direction of the insertion section, the insertion section being configured to be inserted into a tube, a plurality of stiffness variable portions provided in the respective segments and configured to vary stiffness of the respective segments, a state detector configured to detect a shape of the insertion section, a state calculator configured to acquire a shape of the tube at a time when the insertion section advances into the tube, and configured to calculate a relative position of the segment to the tube, based on the shape of the insertion section and the shape of the tube; and a control device configured to control, based on the shape of the tube, the stiffness variable portion provided in the segment which is calculated the relative position to the tube by the state calculator.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1A is a schematic view of a flexible tube insertion apparatus according to a first embodiment of the present invention.

FIG. 1B is a view for describing the flow of control of a stiffness variable portion.

FIG. 3A is a schematic view of a flexible tube insertion apparatus according to a second embodiment of the present invention.

FIG. 3B illustrates a configuration of a start instruction portion of the second embodiment, FIG. 3B being a view for describing the flow of control in the start instruction portion.

FIG. 4 illustrates a configuration of a control device of a third embodiment of the present invention, FIG. 4 being a view for describing the flow of control in the control device.

FIG. 5A is a view for describing that, in a fourth embodiment of the present invention, the stiffnesses of stiffness variable portions are varied from a stiffness variable portion provided in the segment passing through a bent section near an operator toward a stiffness variable portion provided in the segment passing through a bent section away from the operator.

FIG. 5B is a view for describing that, in the fourth embodiment of the present invention, the stiffnesses of stiffness variable portions are varied from a stiffness variable portion provided in the segment passing through a bent section away from an operator toward a stiffness variable portion provided in the segment passing through a bent section near the operator.

FIG. 8A is a view for describing that even if the positions of a plurality of bent sections have shifted in accordance with the insertion of the insertion section, the part where the stiffness varies follows at all times the bent section whose position has shifted.

DETAILED DESCRIPTION OF THE INVENTION

Figure 2A:
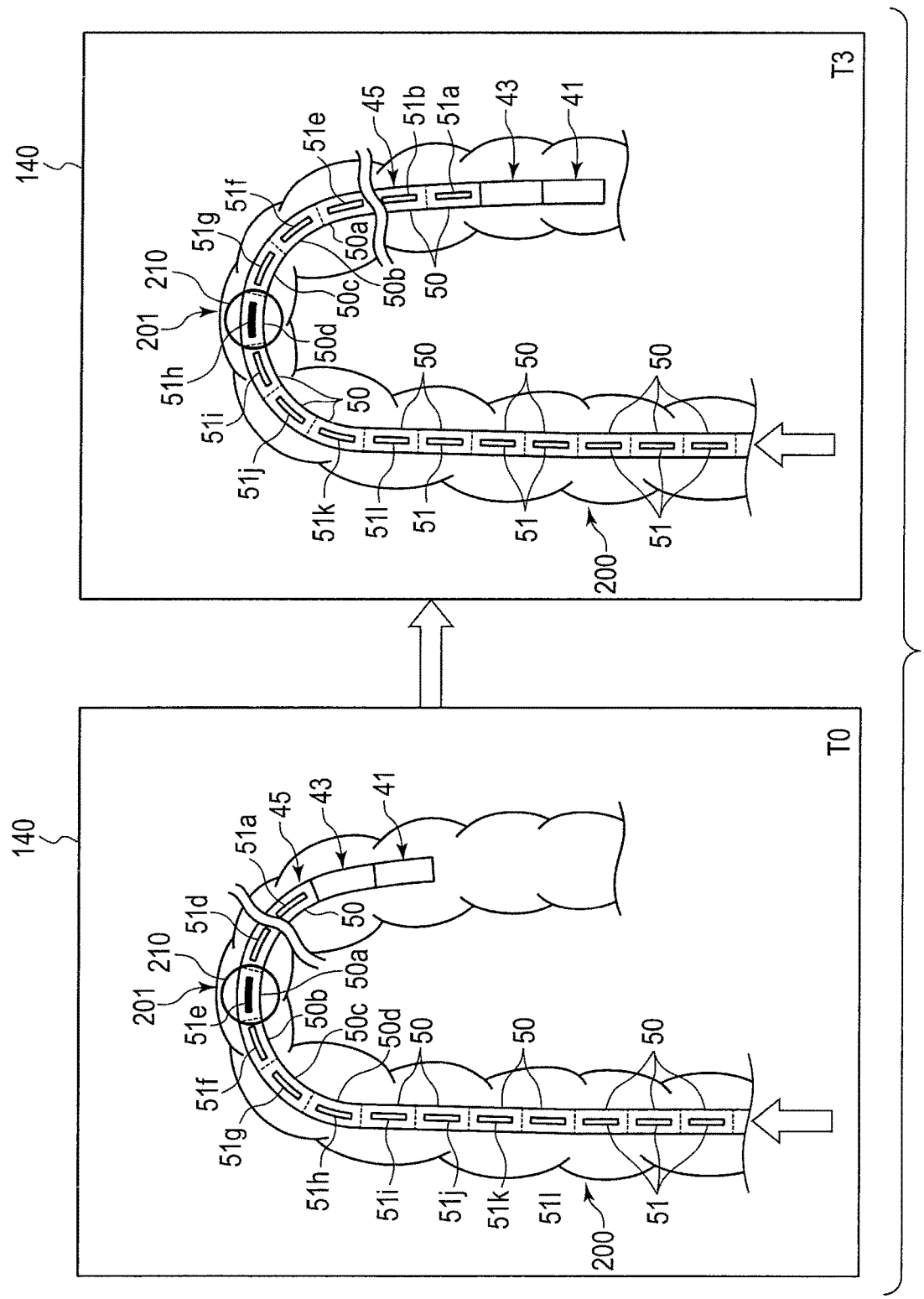
FIG. 2A is a view for describing that the stiffness of a segment at a relative position of the insertion section to a tube varies as the insertion section advances into the tube.

Hereinafter, embodiments of the present invention will be described with reference to the accompanying drawings. Incidentally, the depiction of some of members is omitted in some drawings for the purpose of clearer illustration, for example, as the depiction of a state detector 60 is omitted in FIG. 2A.

[First Embodiment]

A first embodiment will be described with reference to FIG. 1A, FIG. 1B, FIG. 2A, FIG. 2B and FIG. 2C. For the purpose of clearer illustration, FIG. 2C illustrates only segments 50a, 50b and 50c and stiffness variable portions 51e, 51f and 51g, which are necessary for the description.

A flexible tube insertion apparatus (hereinafter referred to as an insertion apparatus 10) as illustrated in FIG. 1A is installed, for example, in an examination room or an operating room. The insertion apparatus 10 includes an endoscope 20 for medical use, a light source device 100 connected to the endoscope 20, and a control device 120 connected to the endoscope 20. The insertion apparatus 10 further includes a display device 140 connected to the control device 120, and a start instruction portion 160 connected to the control device 120.

The endoscope 20 is inserted into a tube 200 such as the large intestine or a tract. The endoscope 20 captures an image of the inside of the tube 200 by an imager (e.g. a CCD or CMOS) of an image pickup unit (not shown).

The light source device 100 emits illumination light which is emitted from the endoscope 20, in order to enable the image pickup unit to perform imaging.

The control device 120 processes the image of the inside of the tube 200, which was captured by the image pickup unit.

The control device 120 controls the endoscope 20 and display device 140. Although the details will be described later, the control device 120 controls the stiffness of an insertion section 40 provided in the endoscope 20.

The display device 140 displays the image which is captured by the image pickup unit and is image-processed by the control device 120. The display device 140 includes, for example, a monitor.

The start instruction portion 160 outputs to the control device 120 an instruction for varying the stiffness of the insertion section 40. The start instruction portion 160 includes, for example, a switch.

The endoscope 20 as illustrated in FIG. 1A is used for describing an example of an insertion device. An example of the insertion device is the endoscope 20 for medical use, as described in the present embodiment, which is inserted into the tube 200 such as the large intestine, but the insertion device does not need to be limited to this example. It is also preferable that the insertion device is an endoscope for industrial use, which is inserted into the tube 200 of an industrial product such as a pipe, or an insertion instrument such as a catheter having only an illumination optical system. When the insertion device is the endoscope 20 for industrial use, the tube 200 is, for example, a conduit. The endoscope 20 may be a forward-viewing endoscope 20 or a side-viewing endoscope 20.

As illustrated in FIG. 1A, the endoscope 20 includes an operation section 30 which is held by an operator, and an insertion section 40 which is inserted into the tube 200.

As illustrated in FIG. 1A, the operation section 30 is provided continuous with a proximal end portion of the insertion section 40. The operation section 30 includes a bending operation portion 31 which operates a bendable portion 43 (to be described later), and a switch 33 which operates respective units such as an image pickup unit. The operation section 30 further includes a universal cord 35, and is connected to the light source device 100 and control device 120 via the universal cord 35.

As illustrated in FIG. 1A, the insertion section 40 is elongated and flexible. The insertion section 40 advances and retreats in the inside of the tube 200 relative to the tube 200. The insertion section 40 includes a distal rigid portion 41, a bendable portion 43 and a flexible tube (flexible tube portion) 45 in the named order from a distal end portion of the insertion section 40 toward the proximal end portion of the insertion section 40. A proximal end portion of the distal rigid portion 41 is coupled to a distal end portion of the bendable portion 43. A proximal end portion of the bendable portion 43 is coupled to a distal end portion of the flexible tube 45. A proximal end portion of the flexible tube 45 is coupled to the operation section 30.

The flexible tube 45 has flexibility and is passively bendable by external force. Thus, the flexible tube 45, which bends by external force, is bendable in accordance with the shape of the tube 200. The distal end portion of the flexible tube 45 may include the distal rigid portion 41 and bendable portion 43.

As illustrated in FIG. 1A, the flexible tube 45 of the insertion section 40 is divided into a plurality of segments 50 which are arranged in a row along the axial direction of the insertion section 40. The segments 50 may function as imaginary regions which do not actually exist, or may function as actually existing structures.

The stiffness of each segment 50 is independently variable by the control of the control device 120. The stiffness of the flexible tube 45 is partly variable by the stiffness of each segment 50 which is independently controlled by the control device 120. Thus, the flexible tube is bendable in accordance with the shape of the tube 200.

Besides, although the flexible tube 45 is divided into the segments 50, the configuration is not limited to this. The insertion section 40 may be divided into segments 50. Thereby, the stiffness of the insertion section 40 is partly variable by the stiffness of each segment 50 which is independently controlled by the control device 120. Thus, the insertion section 40 is configured to be bendable in accordance with the shape of the tube 200.

As illustrated in FIG. 1A, the flexible tube 45 includes the stiffness variable portion 51 whose stiffness is variable. The stiffness variable portion 51 is incorporated in each segment 50. The stiffness variable portions 51 may be incorporated in each of all segments 50, or may be incorporated in only some of the segments 50. In this case, a part where the stiffness variable portions 51 is provided functions as least as the segment 50. Besides, one stiffness variable portion 51 may be incorporated through a plurality of segments 50. The stiffness variable portions 51 may be arranged in one row or in plural rows along an axial direction of the insertion section 40. When the stiffness variable portions 51 are arranged in plural rows, the stiffness variable portions 51, the stiffness variable portions 51 may be provided in the same position in a circumferential direction of the flexible tube 45 such that the stiffness variable portions 51 neighbor each other in the circumferential direction, or may be arranged with a shift in the axial direction of the insertion section 40.

Although not illustrated, the stiffness variable portion 51 is configured to, for example, an actuator which includes a coil pipe formed of a metal wire, and an electroactive polymer artificial muscle (hereinafter referred to as EPAM) which is sealed in the inside of the coil pipe. A center axis of the coil pipe is provided to agree with, or to be in parallel to, a center axis of the insertion section 40. The coil pipe includes electrodes which are provided at both end portions of the coil pipe.

The electrodes are connected to the control device 120 via signal cables (not shown) which are incorporated in the endoscope 20, and electric power is supplied to the electrodes from the control device 120. If a voltage is applied to the EPAM via the electrodes, the EPAM tries to extend or contract along the center axis of the coil pipe. However, the extension and contraction of the EPAM are restricted by the coil pipe. Thereby, the stiffness of the stiffness variable portion 51 varies. Besides, the stiffness of the stiffness variable portion 51 becomes higher as the value of the applied voltage becomes higher. If the stiffness of the stiffness variable portion 51 varies, the stiffness of the segment 50, which incorporates the stiffness variable portion 51, also varies accordingly. In this manner, the stiffness variable portion 51 varies the stiffness of the segment 50 by the variation of stiffness of the stiffness variable portion 51, and partly varies the stiffness of the flexible tube 45 by the variation of stiffness of the segment 50.

In place of the EPAM, a shape memory alloy may be used for the stiffness variable portion 51.

Figure 2B:
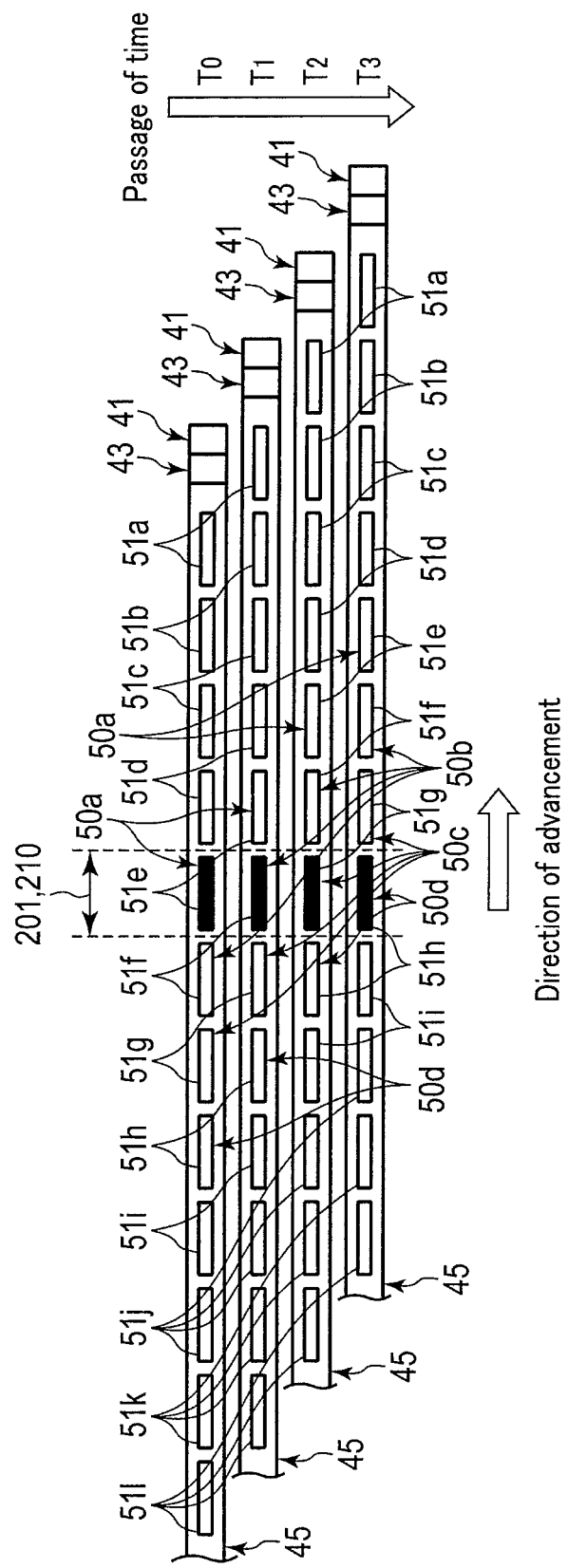
FIG. 2B is a view for describing that the stiffness of the segment at a relative position of the insertion section to the tube varies as the insertion section advances into the tube.
Figure 2C:
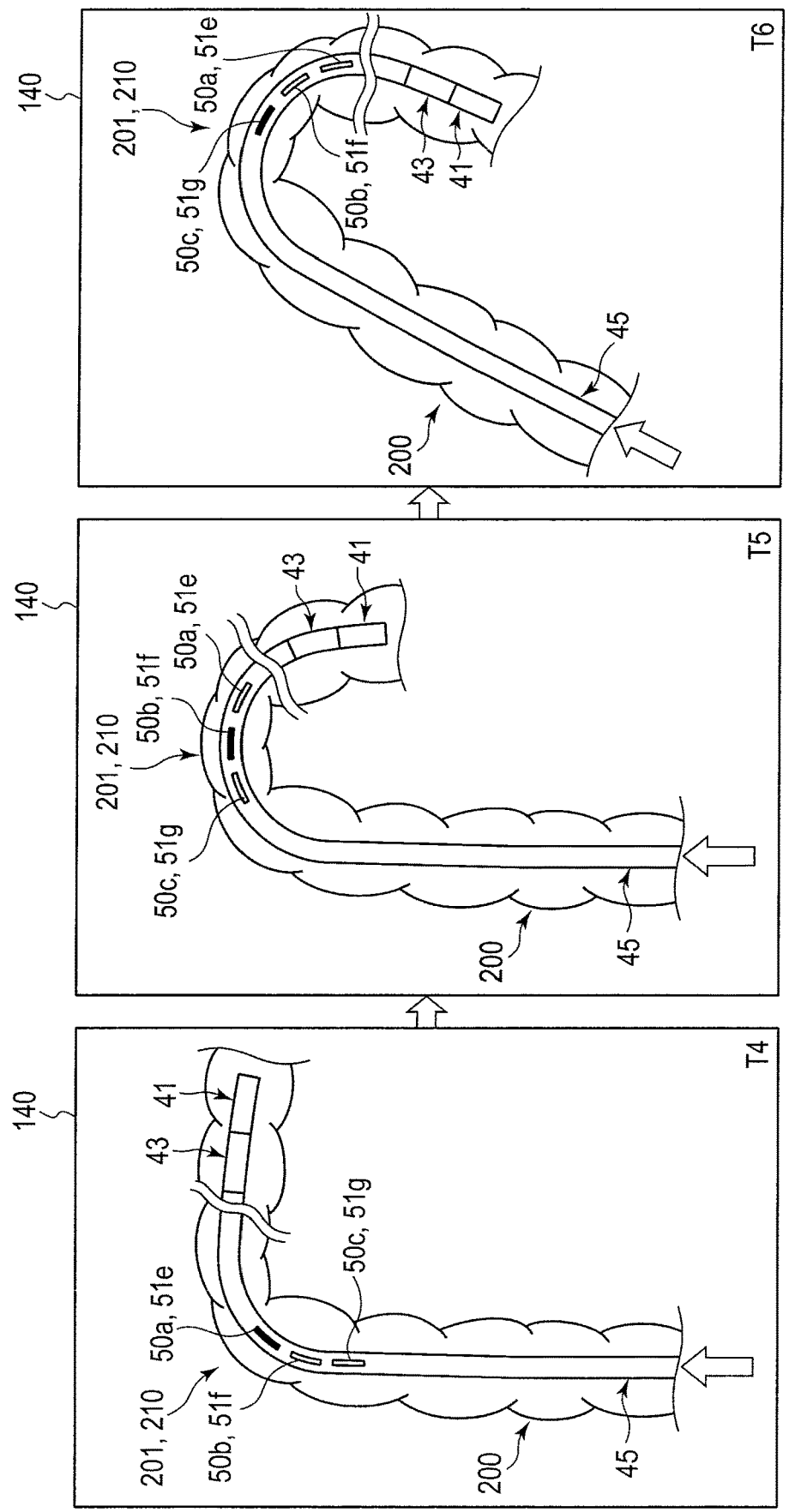
FIG. 2C is a view for describing that even if the position of a bent section shifts in accordance with the insertion of the insertion section, a part where the stiffness varies follows at all times the bent section whose position has shifted.

When the insertion section 40 advances into the tube 200 as illustrated in FIG. 2A and FIG. 2B, the start instruction portion 160, as shown in FIG. 1B, outputs to the control device 120 an instruction (hereinafter referred to as "start instruction") for starting a variation of stiffness of the segment 50 in a relative position of the insertion section 40 to the tube 200.

In the present embodiment, the start instruction portion 160 outputs only the start instruction. The start instruction portion 160 outputs none of a specifying instruction for specifying the stiffness variable portion 51 whose stiffness is to be varied, a stiffness designation instruction for designating the stiffness of the stiffness variable portion 51, and an instruction for restoring the stiffness of the stiffness variable portion 51, whose stiffness varied, to the original stiffness.

As illustrated in FIG. 1A and FIG. 1B, the control device 120 includes a state calculator (state calculation portion) 121 which calculates a state of the insertion section 40, based on a detection result of a state detector (state detection portion) 60 which is provided in the insertion section 40. The control device 120 including the state calculator 121 is configured of, for example, hardware circuitry including an ASIC, etc. The control device 120 may be configured by, for example, a processor including a CPU, etc. When the control device 120 is configured of the processor, an internal memory or external memory (not shown) which the processor can access is disposed. The internal memory or external memory stores a program code which the processor executes, thereby enabling the processor to function as the control device 120. In addition, the control device 120 may be configured using a single processor or by using a plurality of processors. In the case of the latter, the processors can mutually transmit and receive data, and can process the data cooperatively. Besides, in the case of the latter, these processors may be disposed in different housings.

As illustrated in FIG. 1A, the state detector 60 is incorporated in the insertion section 40. It is preferable that the state detector 60 is provided at least in each of the segments 50. In the case of the present embodiment, it is particularly preferable that the state detector 60 is provided at least at a location where the stiffness variable portion 51 is provided.

The state detector 60 detects a state of the insertion section 40 such as a shape of the insertion section 40 and a twist of the insertion section 40. The state detector 60 includes, for example, at least one of a coil which generates a magnetic field, an output portion which outputs electromagnetic waves or ultrasonic waves, an optical fiber sensor, a strain sensor, and an absorption member which absorbs X-rays.

As illustrated in FIG. 1B, the state detector 60 is connected to the state calculator 121, for example, by wire or wirelessly. A detection result detected by the state detector 60 is output to the state calculator 121. After the insertion apparatus 10 is driven, the state detector 60 performs detection (operates) at all times.

The state calculator 121 as illustrated in FIG. 1A and FIG. 1B calculates, based on the detection result of the state detector 60, the state of the insertion section 40 such as the shape of the insertion section 40 and the twist of the insertion section 40. The state calculator 121 further calculates, based on the detection result of the state detector 60, a state of the tube 200 into which the insertion section 40 is inserted, and the position of a bent section 201 in the tube 200.

As illustrated in FIG. 1B, the state calculator 121 is connected to the display device 140. As illustrated in FIG. 2A, based on a calculation result calculated by the state calculator 121, the display device 140 displays the present state of the insertion section 40 in the tube 200. The display is implemented by, for example, three-dimensional display. The operator can monitor the position of the insertion section 40 in the tube 200, based on the state of the insertion section 40 which is displayed on the display device 140.

In the situation in which the position of the insertion section 40 in the tube 200 is being monitored by the operator through the display device 140, the control device 120 controls, as illustrated in FIG. 1B and FIG. 2B, the start of varying of stiffness of the stiffness variable portion 51 provided in the segment 50 at a relative position of the insertion section 40 to the bent section 201 of the tube 200, based on the start instruction that was input from the start instruction portion 160 and the position of the bent section 201 in the tube 200, which was calculated by the state calculator 121. The timing of the control is a timing instructed by the start instruction portion 160 in the state in which the position of the bent section 201 is being calculated, and is a timing at which the start instruction, which is output from the start instruction portion 160 in the state in which the position of the bent section 201 is being calculated, is input to the control device 120. The timing of the control starts at time T0 (see FIG. 2A and FIG. 2B) to be described later, and the control is constantly executed at times T1, T2 and T3 (see FIG. 2A and FIG. 2B) after time T0. The stiffness variable portion 51 that is controlled is the stiffness variable portion 51 which is located in the bent section 201 and indicated in black in FIG. 2A and FIG. 2B.

After the insertion apparatus 10 is driven, the state calculator 121 performs calculation (operates) at all times.

In addition, when the insertion section 40 advances into the tube 200, the state calculator 121 calculates, based on the detection result of the state detector 60, a variation of the state of the tube 200, which occurs in the tube 200.

As illustrated in FIG. 2C, the variation of the state of the tube 200 means, for example, a shift of the position of the tube 200 from a reference, and means, in other words, a movement of the tube 200. The reference means, for example, the state of the tube 200 at a moment when the insertion section 40 has been inserted into the tube 200, or the state of the tube 200 at a predetermined time. The state of the tube 200 varies in real time in accordance with the insertion of the insertion section 40. Besides, the variation of the state of the tube 200 may include an extension/contraction of the tube 200 in accordance with the insertion of the insertion section 40 into the tube 200.

In accordance with the variation of the state of the tube 200, the state of the bent section 201 also varies. As illustrated in FIG. 2C, the variation of the state of the bent section 201 means a shift of the position of the bent section 201, and means, in other words, a movement of the bent section 201. The shift of the position of the bent section 201 also occurs, for example, when the bent section 201 is pushed up by the insertion section 40 or when the tube 200 extends or contracts.

When the state calculator 121 has detected the variation of the state of the tube 200, the control device 120 constantly detects in real time the segment 50 corresponding to the variation of the state of the tube 200 including the bent section 201, based on the variation of the state of the tube 200 including the bent section 201, which was calculated by the state calculator 121. In other words, the control device 120 detects, based on the variation of the state of the tube 200 including the bent section 201, which of the segments 50 passes through the bent section 201 whose position has varied. The detected segment 50 is a segment 50 which passes through the bent section 201 whose position has varied. Specifically, the control device 120 updates the information relating to the segment 50 which passes through the bent section 201 whose position has varied. In addition, the control device 120 constantly controls in real time the variation of stiffness of the stiffness variable portion 51 provided in the detected segment 50. In this manner, when at least one bent section 201 exists in the tube 200 and when there occurs a positional shift of the bent section 201 which is a variation of the state of the tube 200, the control device 120 controls the variation of stiffness of the stiffness variable portion 51 provided in the segment 50 which passes through the bent section 201 in which the positional shift occurred.

After the insertion apparatus 10 is driven, the insertion section 40 is inserted into the tube 200, as illustrated in FIG. 2A. After the insertion apparatus 10 is driven, the state detector 60 detects the state of the insertion section 40. As illustrated in FIG. 1B, the detection result detected by the state detector 60 is output to the state calculator 121. Based on the detection result of the state detector 60, the state calculator 121 calculates the state of the insertion section 40. The state calculator 121 further calculates, based on the detection result of the state detector 60, the state of the tube 200 into which the insertion section 40 is inserted, and the position of the bent section 201 in the tube 200. As illustrated in FIG. 1B and FIG. 2A, based on the calculation result calculated by the state calculator 121, the display device 140 displays the present state of the insertion section 40 in the tube 200. The operator monitors the position of the insertion section 40 in the tube 200, based on the state of the insertion section 40 which is displayed on the display device 140.

As illustrated in FIG. 2A, if the insertion section 40 passes through the bent section 201 of the tube 200, the display device 140 displays, by the state detector 60 and state calculator 121, the shape of the insertion section 40 which bends in accordance with the shape of the bent section 201, and the insertion section 40 which passes through the bent section 201 while bending. This situation is monitored by the operator.

When the insertion section 40 passes through the bent section 201 of the tube 200 and the operator is monitoring, the operator operates the start instruction portion 160. As illustrated in FIG. 1B, the start instruction portion 160 outputs a start instruction to the control device 120.

As illustrated in FIG. 1B, based on the start instruction that was input from the start instruction portion 160 and the position of the bent section 201 in the tube 200, which was calculated by the state calculator 121, the control device 120 controls the start of varying of stiffness of the stiffness variable portion 51 provided in the segment 50 at a relative position of the insertion section 40 to the bent section 201 of the tube 200.

To be more specific, as illustrated in FIG. 2A and FIG. 2B, as the insertion section 40 is further inserted, the absolute part (position) of the insertion section 40, whose stiffness varies, shifts backward. The control device 120 changes (switches) the stiffness variable portion 51 whose stiffness varies, so that a part 210 of the insertion section 40, whose stiffness varies, may not change relative to the bent section 201. At this time, the control device 120 controls the stiffness variable portions 51 so that the stiffness variable portion 51 whose stiffness varies may shift from the stiffness variable portion 51, which is passing through the bent section 201, to the stiffness variable portion 51 which will then pass through the bent section 201. Thus, when the insertion section 40 passes through the bent section 201, the stiffness of the insertion section 40 at the part 210 passing through the bent section 201 will constantly vary. It should suffice if the part 210 includes at least one segment 50.

Specifically, as illustrated in FIG. 2B, it is assumed that stiffness variable portions 51a, 51b, 51c, 51d, 51e, 51f, 51g, 51h, 51i, 51j, 51k and 51l are arranged in the named order from the bendable portion 43 toward the operation section 30.

In this case, at time T0, the stiffness of the stiffness variable portion 51e, which is provided in a segment 50a passing through the bent section 201, varies.

The insertion section 40 is further inserted (the insertion section 40 further advances), and time passes from time T0 to time T1. At time T1, a segment 50b passing through the bent section 201 is not the segment 50a passing through the bent section 201 at time T0, but a segment disposed behind the segment 50a which passed through the bent section 201 at time T0. In addition, the stiffness of the stiffness variable portion 51f, which is provided in this segment 50b and disposed behind the stiffness variable portion 51e, varies.

Similarly, a segment 50c is disposed behind the segment 50b, and a segment 50d is disposed behind the segment 50c. The stiffness variable portion 51g is provided in the segment 50c, and the stiffness variable portion 51h is provided in the segment 50d. If the insertion section 40 is further inserted (the insertion section 40 further advances) and time passes to Time T2, T3, the stiffness of the stiffness variable portion 51g, 51h, which is provided in this segment 50c, 50d, varies.

Thereby, the part 210 whose stiffness varies does not change relative to the bent section 201, and the stiffness of the insertion section 40 at the part 210 passing through the bent section 201 will constantly vary.

Besides, when the insertion of the insertion section 40 is stopped, the stiffness variable portion 51 whose stiffness varies does not change. In other words, the absolute part (position) of the insertion section 40, whose stiffness varies, does not change, and the stiffness of the stiffness variable portion 51, which is always located at the same position relative to the bent section 201 of the tube 200, is varying.

In addition, for example, in the variation of stiffness of the stiffness variable portion 51e and the variation of stiffness of the stiffness variable portion 51f at time T1, the stiffness of the stiffness variable portion 51e gradually decreases and the stiffness of the stiffness variable portion 51f gradually increases. The ratio of the increase is substantially equal to the ratio of the decrease. The increase and decrease may be implemented stepwise or may be implemented linearly. Alternatively, at the same time as the stiffness of the stiffness variable portion 51e instantaneously restores to the original stiffness, the stiffness of the stiffness variable portion 51f may instantaneously increases. This point is similarly applicable to time T2 and Time T3.

Besides, as illustrated in FIG. 2C, for example, at time T4, it is assumed that the stiffness of the stiffness variable portion 51e, which is provided in the segment 50a passing through the bent section 201 and is indicated in black, varies.

When the insertion section 40 further advances into the tube 200 and passes through the bent section 201, it is assumed that the state of the tube 200 at time T5 has changed relative to the state of the tube 200 at time T4. It is also assumed that the position of the bent section 201 at time T5 has thereby shifted relative to the position of the bent section 201 at time T4.

Due to the positional shift, the state of the insertion section 40 changes by the external force which the insertion section 40 receives from the tube 200 including the bent section 201. The state detector 60 detects this changed state of the insertion section 40, and outputs the state of the insertion section 40, which is the detection result, to the state calculator 121. Based on the state of the insertion section 40, the state calculator 121 calculates the state of the tube 200 including the bent section 201. Specifically, based on the state of the insertion section 40, the state calculator 121 constantly calculates in real time the variation of the state of the tube 200 including the bent section 201 due to the insertion of the insertion section 40.

Based on the variation of the state of the tube 200 including the bent section 201, which was calculated by the state calculator 121, the control device 120 constantly detects in real time the segment 50b corresponding to the variation of the state of the tube 200 including the bent section 201. In addition, the control device 120 constantly controls in real time the variation of stiffness of the stiffness variable portion 51f which is provided in the detected segment 50b and is indicated in black.

Thus, at time T5, when the position of the bent section 201 has shifted, the stiffness of the stiffness variable portion 51f, which is provided in the segment 50b passing through the shifted bent section 201, varies.

Besides, when the control device 120 has detected the segment 50b, the control device 120 controls, at time T5, the stiffness variable portion 51e such that the stiffness of the stiffness variable portion 51e, which is provided in the segment 50a passing through the bent section 201 before the variation, becomes the stiffness at time T4.

In the meantime, the control device 120 may control, at time T5, the stiffness variable portion 51e such that the stiffness of the stiffness variable portion 51e restores the initial state. For example, the initial state indicates the stiffness at the moment when the insertion section 40 was inserted into the tube 200. In addition, the control device 120 may control, at time T5, the stiffness variable portion 51e such that the stiffness of the stiffness variable portion 51e at time T5 may differ from the stiffness of the stiffness variable portion 51e at time T4.

Next, when the insertion section 40 further advances into the tube 200 and passes through the bent section 201, it is assumed that the position of the bent section 201 at time T6 has shifted relative to the position of the bent section 201 at time 15. Like the above, when the position of the bent section 201 has shifted, the stiffness of the stiffness variable portion 51g which is provided in the segment 50c passing through the shifted bent section 201 and is indicated in black, varies.

Besides, by the control of the control device 120, the stiffness of the stiffness variable portion 51f at time T6 may be the stiffness at time T5, or may restore to the initial state, or may differ from the stiffness at time T5. The same applies to the stiffness of the stiffness variable portion 51e.

In this manner, when the position of the bent section 201 has shifted in accordance with the insertion of the insertion section 40, the positional shift of the bent section 201 is calculated by the state detector 60 and state calculator 121, based on the state of the insertion section 40, in real time. In addition, the segments 50a, 50b and 50c, which pass through the shifted bent section 201, are constantly detected by the control device 120. Thereby, the part 210 whose stiffness varies follows the shifted bent section 201 at all times. As a result, the part 210 whose stiffness varies does not change relative to the bent section 201, and the stiffness of the insertion section 40 at the part 210 passing through the bent section 201 varies constantly. Besides, the stiffness of the stiffness variable portion 51e, 51f, 51g can be set to a desired value, based on the state of the insertion section 40 and the state of the tube 200.

In the present embodiment, even if the state of the tube 200 varies in accordance with the insertion of the insertion section 40, the stiffness of the insertion section 40 at the part 210 passing through the bent section 201 can constantly be varied at the timing when the start instruction that is output from the start instruction portion 160 is input to the control device 120 or, in other words, the timing when the insertion section 40 passes through the bent section 201. Thus, in this embodiment, the flexible tube 45 can easily be inserted into the bent section 201.

In the present embodiment, even in the situation in which the shape of the tube 200 and the shape of the insertion section 40, which corresponds to the shape of the tube 200, are varying in real time, the stiffness of the insertion section 40 at the part 210 passing through the bent section 201 can constantly be varied at the timing of passing through the bent section 201, without using insertion patterns in the past. Thus, in this embodiment, the flexible tube 45 can easily be inserted into even the bent section 201.

In general, in the endoscopic examination of the large intestine, the stiffness of internal organs disposed near the large intestine and the stiffness of the intestine are different in accordance with patients and the position of disposition of them. Thus, the patterns for enhancing the ease in insertion are not uniquely determined by prerecorded insertion patterns in the past. In the present embodiment, the stiffness of the insertion section 40 at the part 210 passing through the bent section 201 can constantly be varied at the timing of passing through the bent section 201. Thus, in this embodiment, the flexible tube 45 can easily be inserted into even the bent section 201.

In general, as the insertion section 40 advances, the part whose flexibility has varied shifts relative to the bent section 201. Thus, even if the ease in insertion is enhanced by the initially selected insertion pattern, it is possible that the ease in insertion deteriorates at the moment of the shift. In the present embodiment, the control device 120 controls the stiffness variable portions 51 so that the stiffness variable portion 51 whose stiffness varies shift to the stiffness variable portion 51, which is passing through the bent section 201, and shift to the stiffness variable portion 51 which will then pass through the bent section 201. Thus, in this embodiment, the flexible tube 45 can easily be inserted into even the bent section 201.

It is now assumed that there exist a plurality of bent sections 201, and that there exist a plurality of locations where the flexibility of the flexible tube 45 is varied in accordance with a predetermined insertion pattern. In this case, for some operators, a variation in an insertion force amount, which was not experienced in the past, is transmitted to their hands. Consequently, it is possible that the insertion of the insertion section 40 is stopped when the insertion section 40 should be pushed, or conversely it is possible that the insertion section 40 is further inserted when the insertion of the insertion section 40 should be stopped. In this embodiment, the stiffness of the insertion section 40 at the part 210 passing through the bent section 201 can constantly be varied at the timing of passing through the bent section 201. Thus, in this embodiment, the flexible tube 45 can easily be inserted into even the bent section 201.

In the present embodiment, at the timing of passing through bent section 201, the stiffness of the insertion section 40 at the part 210 passing through the bent section 201 can constantly be varied. Thus, in this embodiment, even if the insertion section 40 is erroneously pushed in, it is possible to prevent pushing the intestinal wall, to prevent extension of the bent section 201 and to prevent causing pain to the patient. In this embodiment, the insertion section 40 can safely be inserted without increasing the amount of force for pushing in the insertion section 40.

The variation of the state of the bent section 201 may be defined, by way of example, such that while a first bent section that is an initial one remains, a second bent section that is a new one occurs in accordance with the variation of the shape which is the state of the tube 200.

In this case, at time T4, the stiffness of the stiffness variable portion 51e corresponding to the first bent section is varied. At time T5, the second bent section occurs, and the stiffness of the stiffness variable portion 51f corresponding to the second bent section is varied. At this time, the stiffness variable portion corresponding to the first bent portion keeps the stiffness of the stiffness variable portion 51e at time T4. At time T6, a third bent section occurs, and the stiffness of the stiffness variable portion 51g corresponding to the third bent section is varied. At this time, the stiffness variable portion corresponding to the first bent portion keeps the stiffness of the stiffness variable portion 51e at time T4. The stiffness variable portion corresponding to the second bent portion keeps the stiffness of the stiffness variable portion 51f at time T5.

[Second Embodiment]

Hereinafter, only different points from the first embodiment will be described with reference to FIG. 3A and FIG. 3B. In the present embodiment, the start instruction portion 160 will be described in greater detail than the start instruction portion 160 of the first embodiment.

The start instruction portion 160 includes an operation portion 161 which is operated based on the state of the insertion section 40 that is displayed on the display device 140, and an output portion 163 which outputs a start instruction to the control device 120 when the operation portion 161 was operated.

The operation portion 161 is operated by the operator at a predetermined timing in the state in which the state of the insertion section 40 in the tube 200 displayed on the display device 140 is being monitored by the operator. The operation portion 161 is also a sensing portion which senses the operator's operation.

The operation portion 161 is, for example, a separate body from the endoscope 20, and is provided on the outside of the endoscope 20. In this case, the operation portion 161 is, for example, a footswitch which is operated by the operator. The footswitch is connected to the control device 120, for example, by wire or wirelessly. The operation portion 161 may be a touch panel, or a microphone which collects, for example, a voice uttered by the operator. The touch panel is provided, for example, on the display device 140.

Although not illustrated, the operation portion 161 may be provided, for example, in the endoscope 20. In this case, the operation portion 161 includes the switch 33 or a motion sensor provided in the operation section 30.

The output portion 163 may be configured of, for example, hardware circuitry including an ASIC, etc. The output portion 163 may be configured by, for example, a processor including a CPU, etc. The control device 120 may include the output portion 163.

In the present embodiment, by the operation portion 161 and output portion 163, the start instruction can exactly be output in real time when the insertion section 40 passes through the bent section 201. It is possible to exactly prevent extending the bent section 201 and causing pain to the patient.

[Third Embodiment]

Hereinafter, only different points from the first and second embodiments will be described with reference to FIG. 4. In the present embodiment, the control device 120 will be described in greater detail than the control device 120 of the first embodiment.

The control device 120 further includes a number-of-bends detector (number-of-bends detection portion) 123 which detects, based on the state of the insertion section 40 that is the calculation result of the state calculator 121, the number of at least one or more bent sections 201 (hereinafter referred to as "number of bends") of the tube 200 into which the insertion section 40 is inserted. The number-of-bends detector 123 constantly detects the number of bends during a work of inserting the insertion section 40. The timing when the number-of-bends detector 123 starts detection is a desired timing.

The control device 120 further includes a specifying controller (specifying control portion) 125 which specifies the segment 50 whose stiffness is to be varied, based on the detection result (the number of bent sections 201) of the number-of-bends detector 123 when the start instruction is input to the control device 120, and controls the stiffness variable portion 51 such that the stiffness of the stiffness variable portion 51 provided in the specified segment 50 varies.

The specifying controller 125 is connected to each stiffness variable portion 51 via a signal cable (not shown) incorporated in the inside of the endoscope 20. The specifying controller 125 outputs a start instruction to the specified stiffness variable portion 51 via the signal cable, and controls the stiffness variable portion 51, based on the start instruction.

The state calculator 121, number-of-bends detector 123 and specifying controller 125 are configured of, for example, hardware circuitry including an ASIC, etc. At least one of the state calculator 121, number-of-bends detector 123 and specifying controller 125 may be configured by, for example, a processor including a CPU, etc. When at least one of these is configured of the processor, an internal memory or external memory (not shown) which the processor can access is disposed. The internal memory or external memory stores a program code which the processor executes, thereby enabling the processor to function as at least one of these. In addition, the state calculator 121, number-of-bends detector 123 and specifying controller 125 may be configured by using a single processor or by using a plurality of processors. In the case of the latter, the processors can mutually transmit and receive data, and can process the data cooperatively. Besides, in the case of the latter, these processors may be disposed in different housings.

In the present embodiment, the number of bends can exactly be detected by the number-of-bends detector 123, and all stiffness variable portions 51 corresponding to at least one bent section 201 can specified by the specifying controller 125. Thus, in this embodiment, the stiffness of the insertion section 40 at the part 210 passing through at least one bent section 201 can exactly be varied. Therefore, in this embodiment, the flexible tube 45 can easily be inserted into even the tube 200 including a plurality of bent sections 201.

[Fourth Embodiment]

Hereinafter, only different points from the first, second and third embodiments will be described with reference to FIG. 5A and FIG. 5B. In the present embodiment, the control device 120 will be described in greater detail than the control device 120 of the first embodiment.

When the number of bends is plural, the specifying controller 125 controls the stiffness variable portions 51 such that the stiffnesses of the stiffness variable portions 51 vary in a predetermined order.

For example, as illustrated in FIG. 5A, this order means that the stiffnesses of the stiffness variable portions 51 are varied from the stiffness variable portion 51 provided in the segment 50 passing through the bent section 201 which is near the operator, toward the stiffness variable portion 51 provided in the segment 50 passing through the bent section 201 which is far from the operator.

As illustrated in FIG. 5A, when the number of bends is two, there exist a segment 51a passing through a bent section 201a near the operator, a segment 51b passing through a bent section 201b far from the operator, and stiffness variable portions 51a and 51b provided in the segments 50a and 50b. In this case, the stiffness of the stiffness variable portion 51a varies, and then the stiffness of the stiffness variable portion 51b varies.

As illustrated in FIG. 5A, when the number of bends is three, there exist, furthermore, a segment 50c passing through a bent section 201c which is farther from the operator, and a stiffness variable portion 51c provided in the segment 50c. In this case, the stiffness of the stiffness variable portion 51a varies. Then, the stiffness of the stiffness variable portion 51b varies. Next, the stiffness of the stiffness variable portion 51c varies.

For example, as illustrated in FIG. 5B, the order may mean that the stiffnesses of the stiffness variable portions 51 are varied from the stiffness variable portion 51 provided in the segment 50 passing through the bent section 201 which is far from the operator, toward the stiffness variable portion 51 provided in the segment 50 passing through the bent section 201 which is near the operator.

As illustrated in FIG. 5B, when the number of bends is two, the stiffness of the stiffness variable portion 51b varies, and then the stiffness of the stiffness variable portion 51a varies.

As illustrated in FIG. 5B, when the number of bends is three, the stiffness of the stiffness variable portion 51c varies. Then, the stiffness of the stiffness variable portion 51b varies. Next, the stiffness of the stiffness variable portion 51a varies.

This order is prerecorded in a memory (memory portion) provided in the control device 120. When the number-of-bends detector 123 detected a plural number of bends, the specifying controller 125 outputs start instructions to the stiffness variable portions 51 in accordance with the order recorded in the memory.

In the meantime, this order may discretionarily be designated by the operator, based on the state of the insertion section 40 displayed on the display device 140. For example, by operating the touch panel provided on the display device 140, the operator designates the order of positions for varying stiffnesses, to be more specific, the order of stiffness variable portions 51 whose stiffnesses are varied.

In the present embodiment, by varying the stiffnesses of the stiffness variable portions 51 in the predetermined order and by varying the stiffness of the designated stiffness variable portion 51, the flexible tube 45 can optimally be inserted into the bent section 201 in accordance with the shape of the tube 200 and the situation in which the insertion section 40 is passed through the bent section 201.

Figure 6:
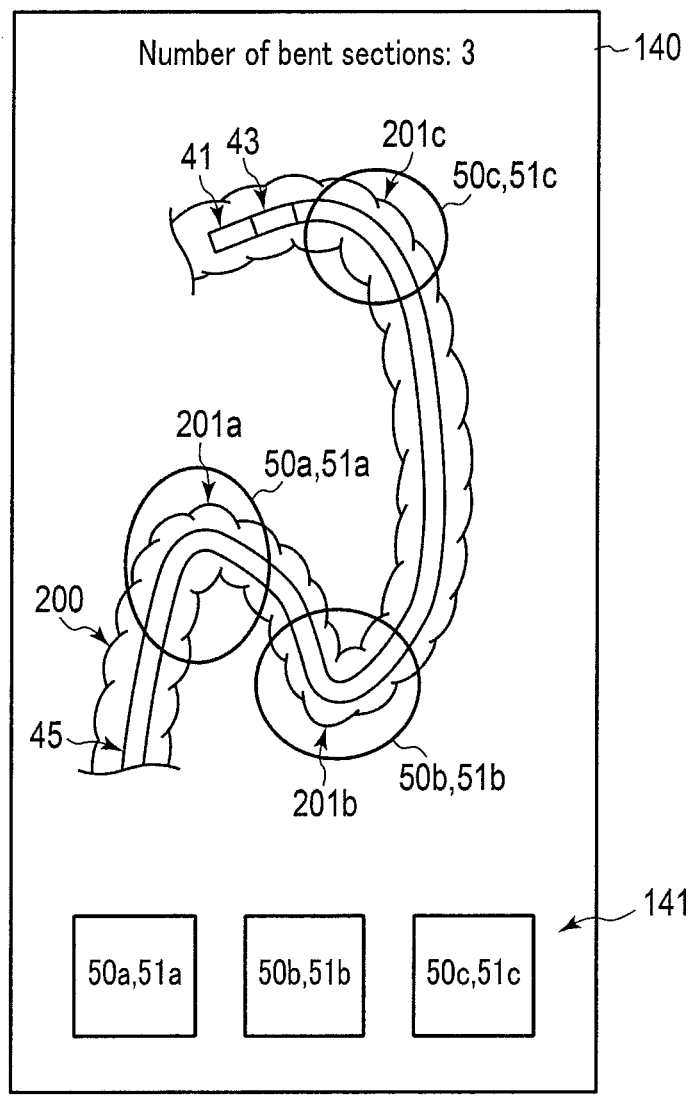
FIG. 6 is a view for describing that the stiffness of a selected stiffness variable portion is varied in a modification of the fourth embodiment of the present invention.

Besides, as a modification of the present embodiment, the stiffnesses of the stiffness variable portions 51 may not necessarily be varied in the order. As illustrated in FIG. 6, based on the state of the insertion section 40 displayed on the display device 140, the specifying controller 125 controls the stiffness variable portions 51 such that the stiffness of the stiffness variable portion 51 provided in a designated segment 50 varies. Thus, for example, by operating a selector (select portion) 141 such as a touch panel provided on the display device 140, the operator selects the position where the stiffness is to be varied, to be more specific, the stiffness variable portion 51 whose stiffness is to be varied.

[Fifth Embodiment]

Figure 7:
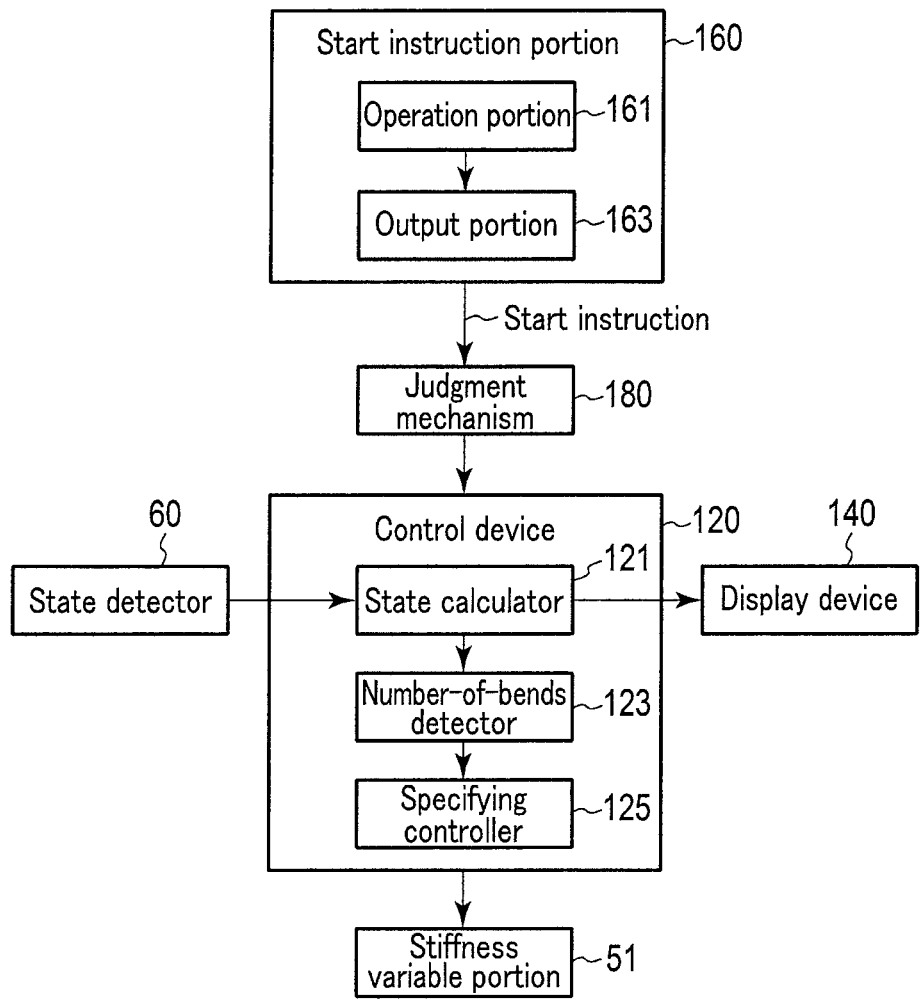
FIG. 7 is a view for describing the flow of control of the stiffness variable portion in accordance with the detection of a stuck state in a fifth embodiment of the present invention.

Hereinafter, only different points from the first, second, third and fourth embodiments will be described with reference to FIG. 7. In the present embodiment, the insertion apparatus 10 will be described in greater detail than the insertion apparatus 10 of the first embodiment.

The control device 120 outputs a start instruction to the stiffness variable portion 51 at a timing instructed by the start instruction portion 160, this timing being a timing at which the start instruction, which is output from the output portion 163, is input to the control device 120. Based on the start instruction, the control device 120 controls the stiffness variable portion 51. However, the control device 120 is not limited to this configuration.

In addition to the above timing, at a timing when the insertion section 40 has lost propulsive force for insertion, the specifying controller 125 of this embodiment outputs the start instruction, and controls the stiffness variable portion 51, based on the start instruction. Thus, the insertion apparatus 10 further includes a judgment mechanism 180 which judges whether the state of the insertion section 40 is a stuck state indicative of a state in which the insertion section 40 has lost propulsive force for insertion, or an insertion state indicative of a state in which the insertion section 40 is being inserted. The judgment mechanism 180 may be configured of, for example, hardware circuitry including an ASIC, etc. The judgment mechanism 180 may be configured by, for example, a processor including a CPU, etc. The control device 120 may include judgment mechanism 180.

For example, if the judgment mechanism 180 judges that an image A captured by the image pickup unit after the passage of a predetermined time does not greatly change from an image B captured before the passage of the predetermined time, the judgment mechanism 180 judges that the state of the insertion section 40 is the stuck state. The judgment mechanism 180 outputs this judgment result to the specifying controller 125, and the specifying controller 125, to which this judgment result was input, controls the stiffness variable portion 51 such that the stiffness of the stiffness variable portion 51 varies.

Besides, if the judgment mechanism 180 judges that the image A has greatly changed from the image B, the judgment mechanism 180 judges that the state of the insertion section 40 is the insertion state. The judgment mechanism 180 outputs this judgment result to the specifying controller 125, and the specifying controller 125, to which this judgment result was input, controls the stiffness variable portion 51 such that the stiffness variable portion 51 stands by. This standby means, for example, that the stiffness of the stiffness variable portion 51 is kept in the initial state (the stiffness of the stiffness variable portion 51 restores to the initial state), or that the stiffness of the stiffness variable portion 51 is kept in the present state (the varied stiffness of the stiffness variable portion 51 is kept).

The judgment mechanism 180 may output this judgment result to the number-of-bends detector 123.

If the judgment mechanism 180 judges that the insertion section 40 is in the stuck state, the number-of-bends detector 123 starts detecting the number of bends.

If the judgment mechanism 180 judges that the insertion section 40 is in the insertion state, the number-of-bends detector 123 stands by for the detection of the number of bends. This standby means that the detected number of bends is maintained, or that the detected number of bends is reset.

Although the judgment mechanism 180 uses images as the basis for judgment, the basis for judgment does not need to be influenced by images. The judgment mechanism 180 may use the detection result of the state detector 60 as the basis for judgment.

In the present embodiment, when the insertion section 40 is in the stuck state, the stiffness of the stiffness variable portion 51 varies. Thus, in the present embodiment, the flexible tube 45 can optimally be inserted into the bent section 201 in accordance with the shape of the tube 200 and the situation in which the insertion section 40 is passed through the bent section 201. In this embodiment, it is possible to prevent pushing the intestinal wall by erroneously pushing in the insertion section 40 despite the insertion section 40 being in the stuck state, to prevent extension of the bent section 201, and to prevent causing pain to the patient. In this embodiment, the insertion section 40 can safely be inserted without increasing the amount of force for pushing in the insertion section 40.

[Sixth Embodiment]

Hereinafter, only different points from the first, second, third, fourth and fifth embodiments will be described with reference to FIG. 8A and FIG. 8B. In the present embodiment, the configurations described in the first, second, third, fourth and fifth embodiments are used, and a description is given of a method in which even when there exist a plurality of bent sections 201 and the positions of the bent sections 201 are shifted in accordance with the insertion of the insertion section, the position of the part 210 whose stiffness varies always follows the shifted bent sections 201.

After the insertion apparatus 10 is driven, the insertion section 40 is inserted into the tube 200. After the insertion apparatus 10 is driven, the state detector 60 detects the state of the insertion section 40. The detection result detected by the state detector 60 is output to the state calculator 121. Based on the detection result of the state detector 60, the state calculator 121 calculates the state of the insertion section 40. Based on the detection result of the state detector 60, the state calculator 121 further calculates the state of the tube 200 into which the insertion section 40 is inserted, and the position of the bent section 201 in the tube 200.

At time T0, the insertion section 40 advances into the tube 200.

At time T1, when the insertion section 40 passes through the bent section 201a, the insertion section 40 enters the stuck state due to the bent section 201a. This state is judged by, for example, the judgment mechanism 180.

At time T2, with the insertion of the insertion section 40, it is assumed that the state of the tube 200 has changed from the state of the tube 200 at time T1, and the position of the bent section 201a has slightly changed from the position of the bent section 201a at time T1. The state detector 60 detects the state of the insertion section 40, and outputs the detection result to the state calculator 121. The state calculator 121 constantly calculates in real time the variation of the position of the bent section 201a, based on the state of the insertion section 40. The control device 120 constantly detects in real time the segment 50a corresponding to the variation of the position of the bent section 201a, based on the variation of the position of the bent section 201a calculated by the state calculator 121. Then, the control device 120 constantly controls in real time the variation of the stiffness of the stiffness variable portion 51a provided in the detected segment 50a.

Thus, at time T2, when the position of the bent section 201a has shifted, the stiffness of the stiffness variable portion 51a provided in the segment 50a, which passes through the shifted bent section 201a, varies.

Figure 8B:
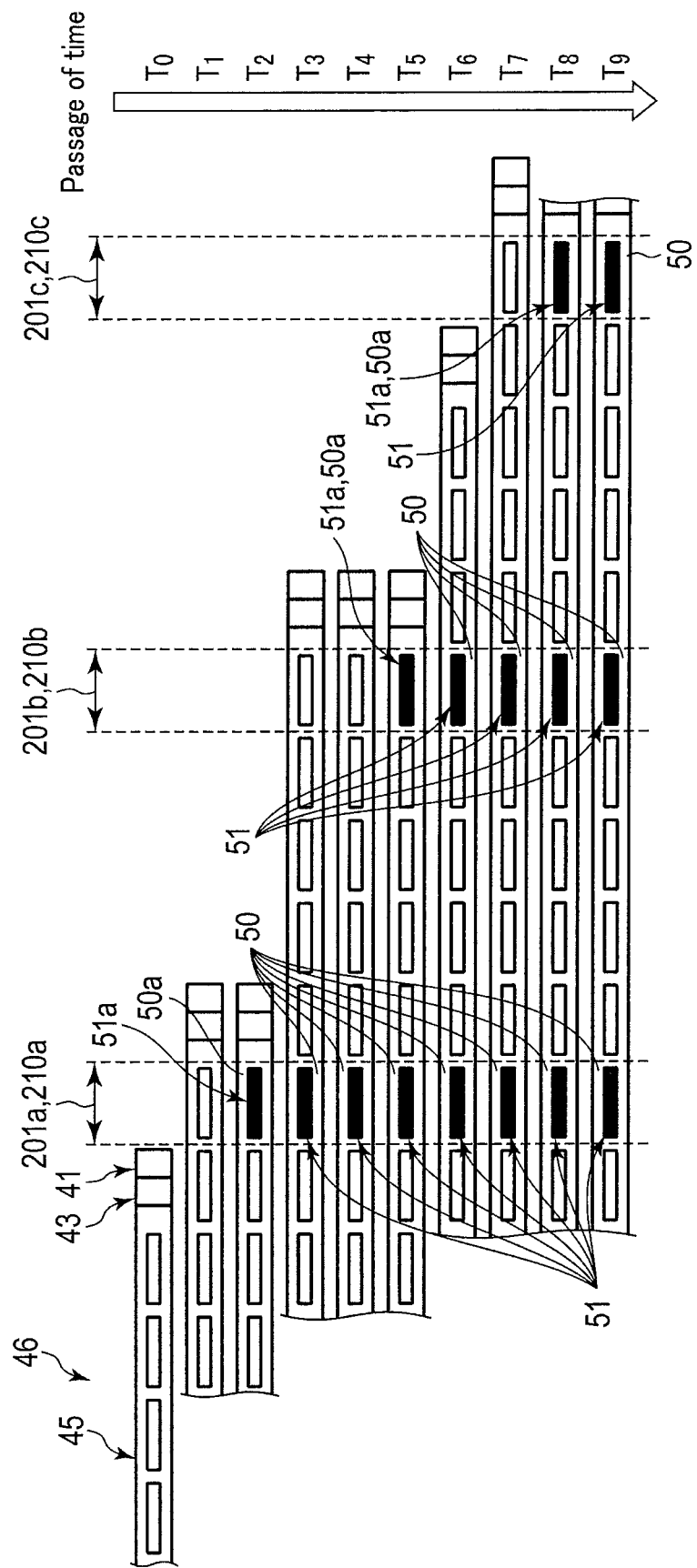
FIG. 8B is a view for describing that the stiffness of the segment at a relative position of the insertion section to the tube varies as the insertion section shown in FIG. 8A advances into the tube.

At time T3 to time T9 after time T2, the stiffnesses of the stiffness variable portions 51, which are provided in the segments 50 passing through the bent section 201a and are indicated in black in FIG. 8B, vary successively. In this manner, the part 210a whose stiffness varies does not change relative to the bent section 201a, and the stiffness of the insertion section 40 at the part 210 passing through the bent section 201a constantly varies.

At time T3, the insertion section 40 further advances in the tube 200. At this time, the stiffness of the insertion section 40 at the part 210 passing through the bent section 201a continues to constantly vary.

At time T4, when the insertion section 40 passes through the bent section 201b, the insertion section 40 enters the stuck state due to the bent section 201b. This state is judged by, for example, the judgment mechanism 180.

At time T5, with the insertion of the insertion section 40, it is assumed that the state of the tube 200 has changed from the state of the tube 200 at time T4, and the position of the bent section 201b has slightly changed from the position of the bent section 201b at time T4. The state detector 60 detects the state of the insertion section 40, and outputs the detection result to the state calculator 121. The state calculator 121 constantly calculates in real time the variation of the position of the bent section 201b, based on the state of the insertion section 40. The control device 120 constantly detects in real time the segment 50a corresponding to the variation of the position of the bent section 201b, based on the variation of the position of the bent section 201b calculated by the state calculator 121. Then, the control device 120 constantly controls in real time the variation of the stiffness of the stiffness variable portion 51a provided in the detected segment 50a.

Thus, at time T5, when the position of the bent section 201b has shifted, the stiffness of the stiffness variable portion 51a provided in the segment 50a, which passes through the shifted bent section 201b, varies.

At time T6 to time T9 after time T5, the stiffnesses of the stiffness variable portions 51, which are provided in the segments 50 passing through the bent section 201b and are indicated in black in FIG. 8B, vary successively. In this manner, the part 210b whose stiffness varies does not change relative to the bent section 201b, and the stiffness of the insertion section 40 at the part 210b passing through the bent section 201b constantly varies.

At time T6, the insertion section 40 further advances in the tube 200. At this time, the stiffness of the insertion section 40 at the parts 210 passing through the bent sections 201a and 201b continues to constantly vary.

At time T7, when the insertion section 40 passes through the bent section 201c, the insertion section 40 enters the stuck state due to the bent section 201c. This state is judged by, for example, the judgment mechanism 180.

At time T8, with the insertion of the insertion section 40, it is assumed that the state of the tube 200 has changed from the state of the tube 200 at time T7, and the position of the bent section 201c has slightly changed from the position of the bent section 201c at time T7. The state detector 60 detects the state of the insertion section 40, and outputs the detection result to the state calculator 121. The state calculator 121 constantly calculates in real time the variation of the position of the bent section 201c, based on the state of the insertion section 40. The control device 120 constantly detects in real time the segment 50a corresponding to the variation of the position of the bent section 201c, based on the variation of the position of the bent section 201c calculated by the state calculator 121. Then, the control device 120 constantly controls in real time the variation of the stiffness of the stiffness variable portion 51a provided in the detected segment 50a.

Thus, at time T8, when the position of the bent section 201c has shifted, the stiffness of the stiffness variable portion 51a provided in the segment 50a, which passes through the shifted bent section 201c, varies.

At time T9 after time T8, the stiffness of the stiffness variable portion 51, which is provided in the segment 50 passing through the bent section 201c and is indicated in black in FIG. 8B, varies. In this manner, the part 210c whose stiffness varies does not change relative to the bent section 201c, and the stiffness of the insertion section 40 at the part 210c passing through the bent section 201c constantly varies.

In this manner, when there exist a plurality of bent sections 201a, 201b and 201c and a positional shift which is the variation of the state of the tube 200 occurs in each of the bent sections 201a, 201b and 201c, the control device 120 controls the variations of stiffnesses of the stiffness variable portions 51 provided in the segments 50 passing through the bent sections 201a, 201b and 201c in which positional shifts have occurred.

Thereby, in the present embodiment, with the insertion of the insertion section 40, even if the positions of the plural bent sections 201 have shifted, the stiffness of the insertion section 40 at the parts 210 passing through the bent sections 201 can constantly be varied. Thus, in this embodiment, the flexible tube 45 can easily be inserted into even the bent section 201.

Besides, in the present embodiment, for example, the stiffnesses of the stiffness variable portions 51, which are provided in the segments 50 passing through the bent sections 201a and 201b and are indicated in black in FIG. 8B, continue to vary. However, the embodiment does not need to be limited to this. For example, as in the fourth embodiment, the specifying controller 125 may control the stiffness variable portions 51 such that the stiffnesses of the stiffness variable portions 51 vary in a predetermined order. Alternatively, based on the state of the insertion section 40 displayed on the display device 140, the specifying controller 125 may control the stiffness variable portions 51 such that the stiffness of the stiffness variable portion 51 provided in a designated segment 50 varies.

In addition, in the present embodiment, the stuck state which the judgment mechanism 180 judges may include, for example, not only a complete stop state in which the insertion of the insertion section 40 completely stops, but also a decreased state in which the ease in insertion of the insertion section 40 has decreased. The complete stop state means that there is no change of the above-described image A from the image B captured before the passage of the predetermined time. The decreased state means that there is no great change of the above-described image A from the image B captured before the passage of the predetermined time. The decreased state means, for example, a difficulty in insertion. The decreased state means, for example, a state occurring due to extension of the tube 200 when the tube 200 extends in accordance with the insertion of the insertion section 40. The degree of the change of the image A from the image B in the decreased state can be set, for example, to a desired value by the control device 120.

The present invention is not limited directly to the above-described embodiments. At the stage of practicing the invention, the structural elements maybe modified and embodied without departing from the spirit of the invention. Various inventions may be made by suitably combining a plurality of structural elements disclosed in the embodiments.

What is claimed is:

1. A flexible tube insertion apparatus comprising:
    an insertion section including a plurality of segments arranged along an axial direction of the insertion section, the insertion section being configured to be inserted into a body lumen;
    an actuator provided in each segment of the plurality of segments, each actuator being configured to vary a stiffness of a respective segment, the stiffness being a resistance to bending;
    a state sensor configured to detect a shape of the insertion section; and
    a controller configured to:
        acquire a shape of the body lumen at a time when the insertion section advances into the body lumen;
        calculate a position of a segment of the plurality of segments relative to the body lumen, based on the detected shape of the insertion section and the acquired shape of the body lumen; and
        vary, based on the acquired shape of the body lumen, the stiffness in the actuator corresponding to the calculated position of the segment.

2. The flexible tube insertion apparatus according to claim 1, wherein when the controller detects that the body lumen includes a first bent section and a second bent section,
    the controller varies a first stiffness in a first actuator and varies a second stiffness in a second actuator such that the second actuator varies a stiffness of a second segment of the plurality of segments located within the second bent section after the first actuator varies a stiffness of a first segment of the plurality of segments located within the first bent section.

3. The flexible tube insertion apparatus according to claim 1, wherein the controller is further configured to determine when a state of the insertion section is a stuck state indicative of a state in which the insertion section has lost propulsive force for insertion, or when the insertion section is in an insertion state indicative of a state in which the insertion section is being inserted, wherein when the state of the insertion section is determined to be in the stuck state, the controller varies the stiffness of the actuator such that the actuator varies the stiffness of the segment, and when the state of the insertion section is determined to be in the insertion state, the stiffness of the actuator is maintained in a present state.

4. The flexible tube insertion apparatus according to claim 1, wherein the controller is configured to control the stiffness of the actuator such that when a positional shift of a bent section of the body lumen is detected, the stiffness of the actuator is varied for the segment passing through the bent section in which the positional shift occurred.

5. The flexible tube insertion apparatus according to claim 1, wherein the controller is configured to vary the stiffness of the actuators such that when an occurrence of a positional shift of each of bent sections of the body lumen is detected, the controller varies the stiffness in the actuators of the segments located within the bent sections in which the positional shift occurred in a predetermined order.

* * * * *